(12) United States Patent
Fair et al.

(10) Patent No.: US 11,655,449 B2
(45) Date of Patent: May 23, 2023

(54) CULTURE CONDITIONS TO PROLONG/ENHANCED ENDODERMAL CELL TYPE FOR CELL TRANSPLANTATION

(71) Applicant: BOARD OF REGENTS, THE UNIVERSITY OF TEXAS SYSTEM, Austin, TX (US)

(72) Inventors: Jeffrey Fair, Galveston, TX (US); William Sam Fagg, Galveston, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 313 days.

(21) Appl. No.: 16/891,856

(22) Filed: Jun. 3, 2020

(65) Prior Publication Data

US 2020/0377853 A1 Dec. 3, 2020

Related U.S. Application Data

(60) Provisional application No. 62/856,505, filed on Jun. 3, 2019.

(51) Int. Cl.
*C12N 5/074* (2010.01)

(52) U.S. Cl.
CPC ........ *C12N 5/0607* (2013.01); *C12N 2500/30* (2013.01); *C12N 2501/15* (2013.01); *C12N 2501/16* (2013.01); *C12N 2506/09* (2013.01); *C12N 2533/52* (2013.01)

(58) Field of Classification Search
CPC .............. C12N 5/0607; C12N 2500/30; C12N 2501/15; C12N 2501/16; C12N 2533/52
See application file for complete search history.

(56) References Cited

U.S. PATENT DOCUMENTS

2015/0329821 A1* 11/2015 Ang .................... C12N 5/0603
435/366

OTHER PUBLICATIONS

Fagg, et al., Magnetic Targeting of Stem Cell Derivatives Enhances Hepatic Engraftment into Structurally Normal Liver, Cell Transplantation, 2017, vol. 26(12), 1868-1877.
Fair, et al., "Correction of factor IX deficiency in mice by embryonic stem cells differentiated in vitro", PNAS, Feb. 28, 2005, vol. 102, No. 8, pp. 2958-2963.
Loh, et al., "Efficient Endoderm Induction from Human Pluripotent Stem Cells by Logically Directing Signals Controlling Lineage Bifurcations", Cell Stem Cell Resource, Feb. 6, 2014, Elsevier Inc. 237-252.

* cited by examiner

*Primary Examiner* — Kara D Johnson
(74) *Attorney, Agent, or Firm* — Edwin S. Flores; Daniel J. Chalker; Chalker Flores, LLP (57) ABSTRACT

The present invention includes a method of preparing differentiated endodermal cells comprising growing human pluripotent stem cells (hPSC) under serum free conditions for 3 days on a layer of fibronectin or a gelatinous protein layer in the presence of high activin/TGF-β with a GSK3 inhibitor and a PI3K/mTORC inhibitor in a basal differentiation medium; adding a knock out serum replacement to the media starting on day 4 through day 7; and harvesting the endodermal cells grown therein.

20 Claims, 6 Drawing Sheets

CULTURE CONDITIONS TO PROLONG/ENHANCED ENDODERMAL CELL TYPE FOR CELL TRANSPLANTATION

CROSS-REFERENCE TO RELATED APPLICATIONS

This application claims priority to U.S. Provisional Application Ser. No. 62/856,505, filed Jun. 3, 2019, the entire contents of which are incorporated herein by reference.

TECHNICAL FIELD OF THE INVENTION

The present invention relates in general to the field of cell culture, and more particularly, to optimized culture conditions to prolong/enhanced endodermal cell type for cell transplantation.

STATEMENT OF FEDERALLY FUNDED RESEARCH

Not Applicable.

INCORPORATION-BY-REFERENCE OF MATERIALS FILED ON COMPACT DISC

Not Applicable.

BACKGROUND OF THE INVENTION

Without limiting the scope of the invention, its background is described in connection with cell culture conditions.

Human cells can be differentiated from pluripotent sources to create cells with endodermal gene expression, and have been shown to repopulate liver tissue for potential therapeutic use. A significant problem with this approach is that in vitro differentiation moves forward in the window by which transplantation may be possible might be quite small as in 12 to 24 hours.

One such method is taught by Loh, et al., "Efficient endoderm induction from human pluripotent stem cells by logically directing signals controlling lineage bifurcations," Cell Stem Cell. 2014 Feb. 6; 14(2):237-52. Epub 2014 Jan. 9. These authors teach that human pluripotent stem cell (hPSC) differentiation typically yields heterogeneous populations by selecting signals that drive induction and anterior-posterior patterning of definitive endoderm to cause endoderm differentiation. BMP and Wnt initially specified an anterior primitive streak (progenitor to endoderm), yet, 24 hr later, these agents suppressed endoderm and induced mesoderm. At lineage bifurcations, cross-repressive signals separated mutually exclusive fates; TGF-β and BMP/MAPK respectively induced pancreas versus liver from endoderm by suppressing the alternate lineage. The authors then systematically blockaded alternate fates throughout multiple consecutive bifurcations, thereby efficiently differentiating multiple hPSC lines exclusively into endoderm and its derivatives. The inventors show comprehensive transcriptional and chromatin mapping of highly pure endodermal populations to reveal that endodermal enhancers existed in a surprising diversity of "pre-enhancer" states before activation, reflecting the establishment of a permissive chromatin landscape as a prelude to differentiation. However, using the methodology taught, progenitor cells began to differentiate within 24 hours.

However, a need remains for novel compositions and method for long-term preservation and growth of cells available for transplantation.

SUMMARY OF THE INVENTION

In one embodiment, the present invention includes a method of preparing differentiated endodermal cells comprising: growing human pluripotent stem cells (hPSC) under serum free conditions for 3 days on a layer of fibronectin or a gelatinous protein layer in the presence of high activin/TGF-β with a GSK3 inhibitor and a PI3K/mTORC inhibitor in a basal differentiation medium; adding a knock out serum replacement to the media starting on day 4 through day 7; and harvesting the endodermal cells grown therein. In one aspect, the GSK3 inhibitor is 6-((2-((4-(2,4-Dichlorophenyl)-5-(4-methyl-1H-imidazol-2-yl)pyrimidin-2-yl)amino)ethyl)amino)nicotinonitrile (CHIR99021). In another aspect, the PI3K/mTORC inhibitor is 3-(4-morpholinopyrido[3',2':4,5]furo[3,2-d]pyrimidin-2-yl)phenol (PI-103). In another aspect, the method further comprises the step of changing the media daily during days 1 to 3, days 4 to 7, or both. In another aspect, the basal differentiation media comprises 50% IMDM and 50% F12 supplemented with 1 mg/mL polyvinyl alcohol, 1% v/v lipids, 450 DM monothioglycerol, 0.7 μg/mL insulin), and 15 μg/mL transferrin. In another aspect, the GSK3 inhibitor is maintained in the media after day 1. In another aspect, the endodermal cells differentiated have change in the MIXL1 phenotype after day 7. In another aspect, the e endodermal cells are transplant competent after 4, 5, 6, or 7 days. In another aspect, the method further comprises the step of transplanting the differentiated endodermal cells into the liver, lung, pancreas, thyroid, or bladder. In another aspect, the differentiated endodermal cells are liver, lung, pancreas, thyroid, or bladder cells. In another aspect, the animal is a human.

In another embodiment, the present invention includes a method of transplanting endodermal cells into an animal comprising: identifying an animal in need of endodermal cell transplantation; growing human pluripotent stem cells (hPSC) under serum free conditions for 3 days on a layer of fibronectin or a gelatinous protein layer in the presence of high activin/TGF-β with a GSK3 inhibitor and a PI3K/mTORC inhibitor in a basal differentiation medium; adding a knock out serum replacement to the media starting on day 4 through day 7; harvesting the endodermal cells grown therein; and transplanting the endodermal cells into the animal. In one aspect, the GSK3 inhibitor is 6-((2-((4-(2,4-Dichlorophenyl)-5-(4-methyl-1H-imidazol-2-yl)pyrimidin-2-yl)amino)ethyl)amino)nicotinonitrile (CHIR99021). In another aspect, the PI3K/mTORC inhibitor is 3-(4-morpholinopyrido[3',2':4,5]furo[3,2-d]pyrimidin-2-yl)phenol (PI-103). In another aspect, the method further comprises the step of changing the media daily during days 1 to 3, days 4 to 7, or both. In another aspect, the basal differentiation media comprises 50% IMDM and 50% F12 supplemented with 1 mg/mL polyvinyl alcohol, 1% v/v lipids, 450 DM monothioglycerol, 0.7 μg/mL insulin), and 15 μg/mL transferrin. In another aspect, the GSK3 inhibitor is maintained in the media after day 1. In another aspect, the endodermal cells differentiated have change in the MIXL1 phenotype after day 7. In another aspect, the endodermal cells are transplant competent after 4, 5, 6, or 7 days. In another aspect, the differentiated endodermal cells are transplanted into liver, lung, pancreas, thyroid, or bladder. In another aspect, the differentiated endodermal cells are liver, lung, pancreas, thyroid, or bladder cells. In another aspect, the animal is a human.

In another embodiment, the present invention includes a method of preparing differentiated endodermal cells made by growing human pluripotent stem cells (hPSC) under serum free conditions on a layer of fibronectin or a gelatinous protein layer in the presence of high activin/TGF-β with a GSK3 inhibitor and a PI3K/mTORC inhibitor in a basal differentiation medium followed and adding a knock out serum replacement to the media the improvement comprising: maintaining the GSK3 inhibitor past day 1 to day 3; and adding the knock out serum replacement to the media starting at day 4 of culture, wherein the differentiated endodermal cells. In one aspect, the differentiated endodermal cells are liver, lung, pancreas, thyroid, or bladder cells. In another aspect, the differentiated endodermal cells are transplanted into liver, lung, pancreas, thyroid, or bladder.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not limit the invention, except as outlined in the claims.

An example of a basal differentiation medium for use with the present invention is a CDM2 basal differential medium that includes 50% IMDM (Gibco) and 50% F12 (Gibco), which many be supplemented with one or more of the following: polyvinyl alcohol (Sigma, A1470 or Europa Bioproducts, EQBAC62), chemically-defined lipid concentrate (Gibco, 11905-031), 450 DM monothioglycerol (Sigma, M6145), insulin (Roche, 1376497) and transferrin (Roche, 652202), which is then filtered (22 μm filter, Millipore) to make a sterile medium. Other components for use with the present invention include, e.g., human fibronectin (Millipore, FC010) or a gelatinous protein matrix such as Matrigel (BD Biosciences), DMEM/F12 (Gibco), Activin A (100 ng/mL, R&D Systems), CHIR99021 (2 μM, Stemgent), PI-103, LDN-193189/DM3189 (250 nM, Stemgent), KNOCKOUT™ Serum Replacement (KOSR)(Gibco).

Endodermal precursors (EP), derived in vitro from mouse pluripotent stem cell (PSC) sources, have proven capable of clinically useful engraftment in the unmodified (quiescent) liver parenchyma. Recent data demonstrate that endodermal lineage gene expression and high proliferation rate are necessary for engraftment in the quiescent liver parenchyma. the in vivo engraftment. [1,2] The human analogue of the EP (hEP) would be useful as wild type gene vector for critical replacement of specific genetic metabolic deficiencies. However in current iterations, the forward differentiation window for hEPs is quite short (<24), limiting the time window and available transplantable cell numbers. Here, the inventors describe conditions that can derive and maintain hEPs in a stable gene expression program for 5 days, significantly increasing the total cell number while maintaining characteristics required for robust engraftment.

Human PSC are maintained in feeder-free conditions and differentiated with extended EP (eEP) culture modification that started with an "SR1" endoderm culture recipe3 for three days, followed by the addition of 10% KNOCKOUT™ serum replacement from day 4 through day 7 (KNOCKOUT™ Serum Replacement (KOSR)(Gibco)). As used herein, an "SR1" endoderm culture recipe is a basal differentiation medium such as a CDM2 medium that includes 1 mg/mL polyvinyl alcohol (Sigma, A1470 or Europa Bioproducts, EQBAC62), 1% v/v chemically-defined lipid concentrate (Gibco, 11905-031), 450 DM monothioglycerol (Sigma, M6145), 0.7 μg/mL insulin (Roche, 1376497) and 15 μg/mL transferrin, a layer of fibronectin or a gelatinous protein layer coated on the well for cell culture, in the presence of high activin/TGF-β with a GSK3 inhibitor and a PI3K/mTORC inhibitor. SR1 Gene expression analysis was performed by RT-qPCR, with surface marker and proliferation analyses ongoing. Early timepoints after cell transplantation to the liver were monitored using bioluminescence-based in vivo imaging with the IVIS.

Figure 1A:
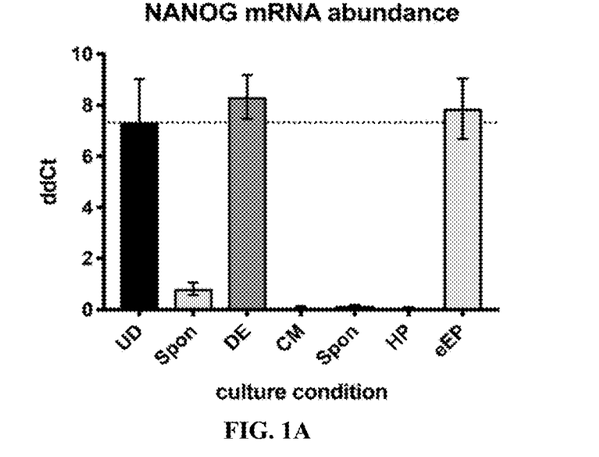
FIGS. 1A to 1O show selected gene expression profiles by the culture conditions of the present invention.
Figure 1B:
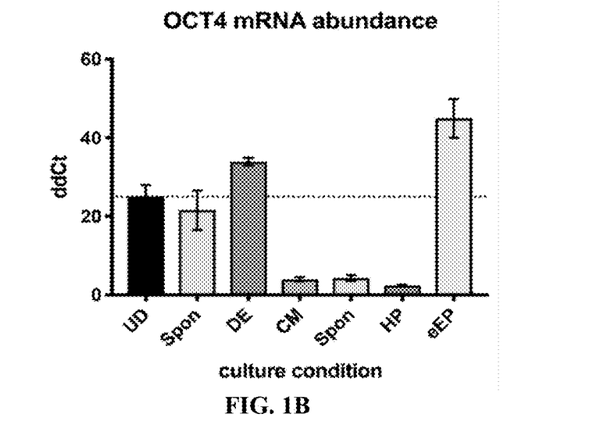
Figure 1C:
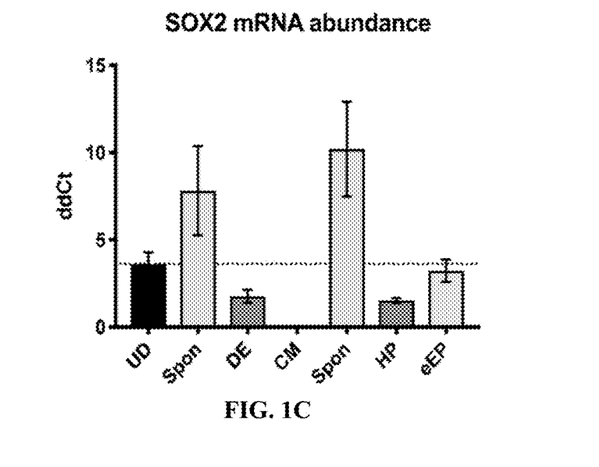
Figure 1D:
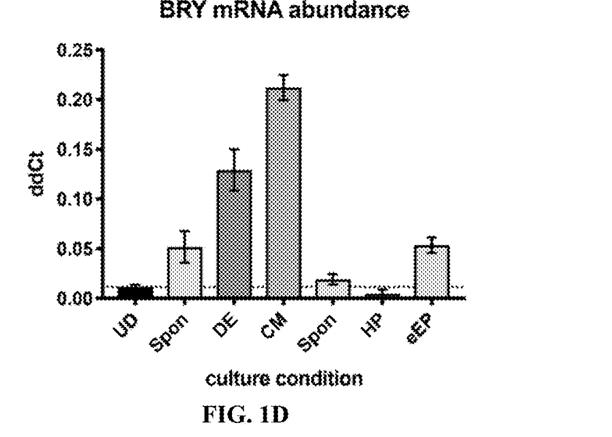
Figure 1E:
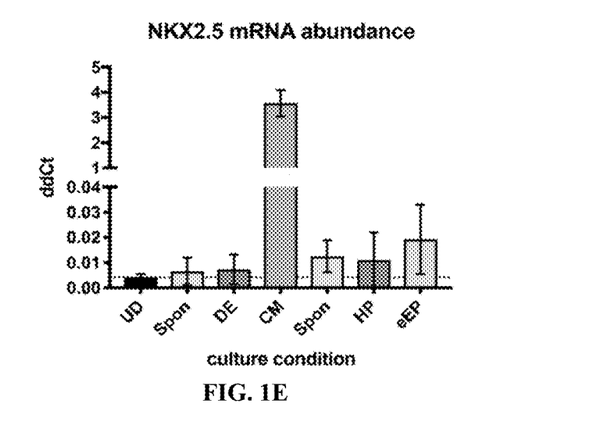
Figure 1F:
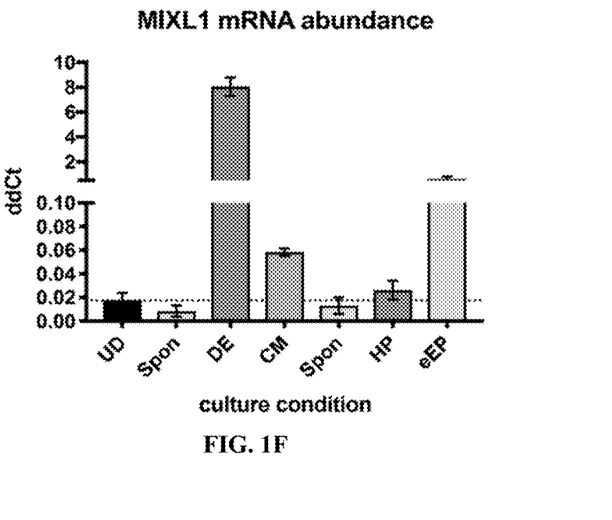
Figure 1G:
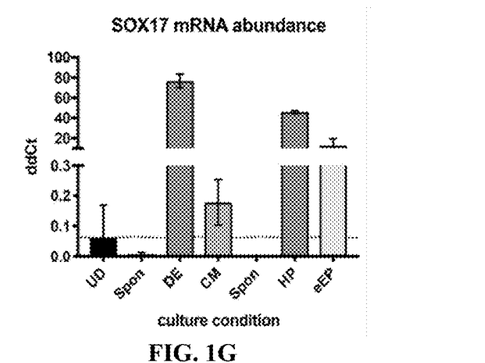
Figure 1H:
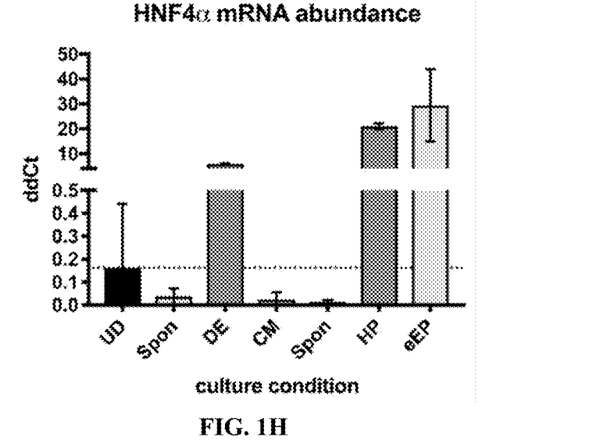
Figure 1I:
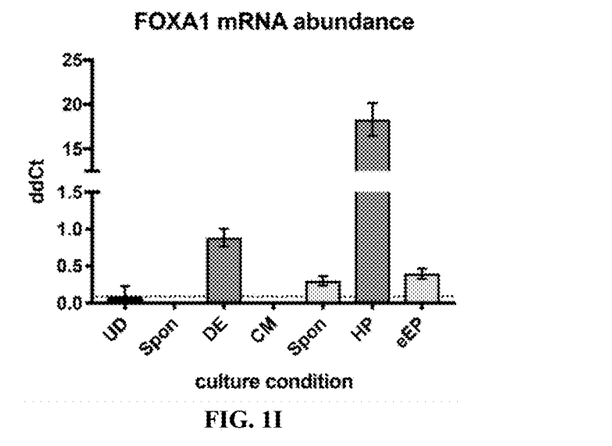
Figure 1J:
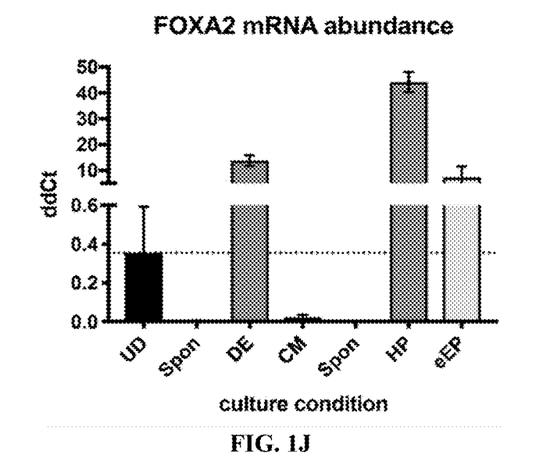
Figure 1K:
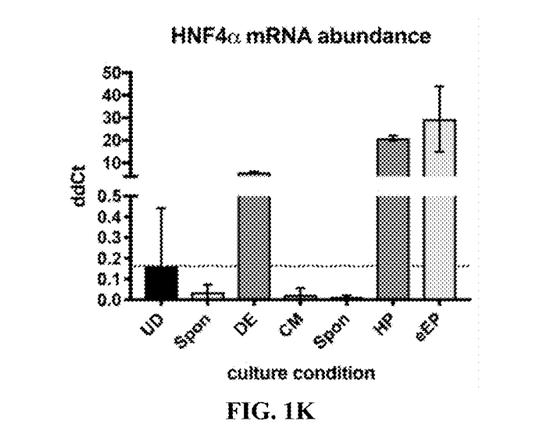
Figure 1L:
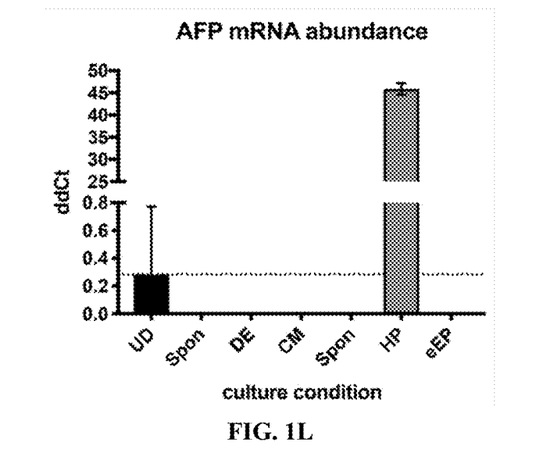
Figure 1M:
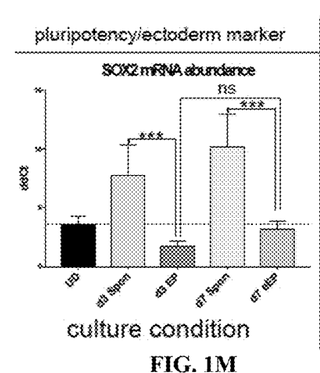
Figure 1N:
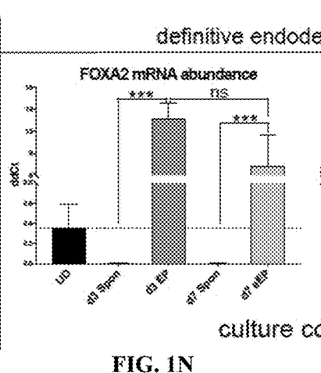
Figure 1O:
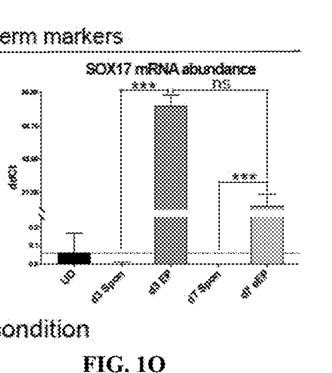

FIGS. 1A to 1O show selected gene expression profiles by the culture conditions of the present invention. RNAs extracted from undifferentiated human iPSCs (UD), day 3 spontaneously differentiated (spon), day 3 endoderm progenitors (EP), day 7 spon, or day 7 extended EP (eEP). FIGS. 1M-1O summarize the results for gene expression profiles measured for respective biomarker abundance by RT-qPCR (ns=not significant, *** means P<0.001 by ordinary one-way ANOVA). It was found that the cells grown under these conditions were able to divide (thus increasing the total number of cells for transplantation), and were able to successfully transplant into a host animal.

Figure 2:
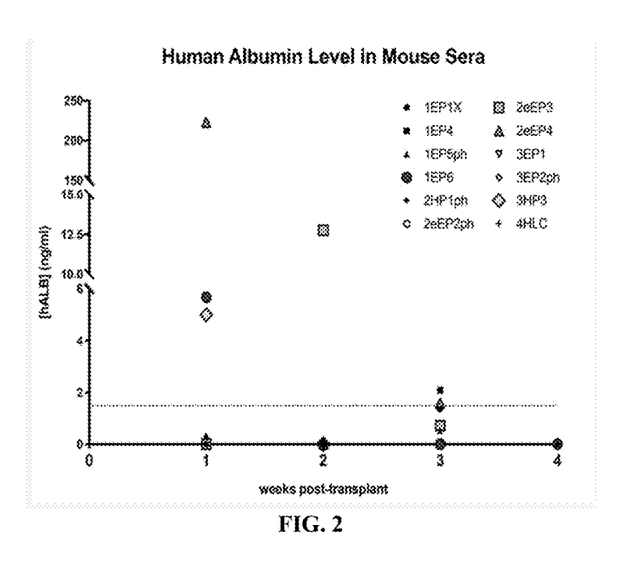
FIG. 2 shows the human albumin level in mouse sera for the listed markers in mice receiving hEP and HeEp transplants.

FIG. 2 shows the human albumin level in mouse sera in mice transplanted with the listed cells. FIG. 2 shows the results for serum extracted from immunocompromised mice receiving human day 3 EP or day 7 eEP transplant either without or with partial hepatectomy (+PH) was tested for human albumin (a hepatocyte biomarker) concentration by ELISA. Baseline level of detection above background is denoted by dashed line.

Figure 3:
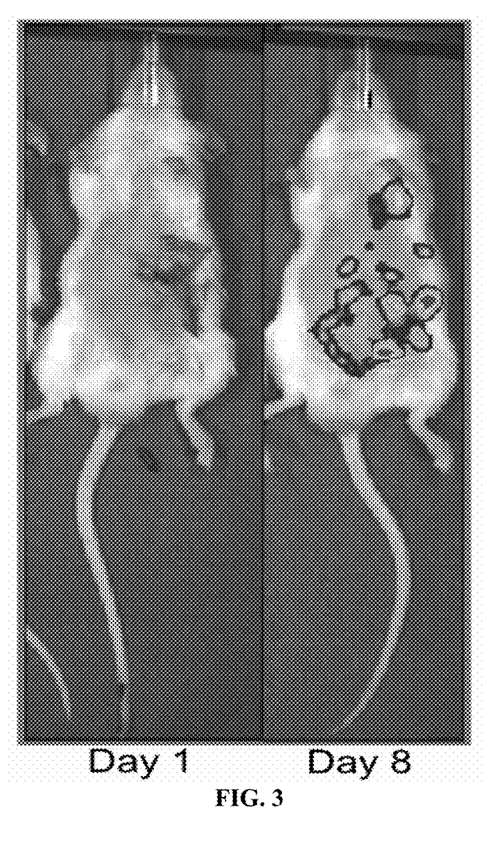
FIG. 3 shows in vivo imaging of immunocompromised mouse receiving eEP d7. Luciferase signal imaged by IVIS system. Mouse is same as denoted eEP2 in FIG. 2.

FIG. 3 shows in vivo imaging of immunocompromised mouse receiving eEP d7. Luciferase signal imaged by IVIS system. Mouse is same as denoted eEP2 in FIG. 2. In vivo imaging of an immunocompromised mouse receiving day 7 differentiated human extended endoderm progenitor (eEP) cell transplant. Luciferase signal is imaged by the IVIS system and the mouse shown here is the same animal denoted as "eEP2" in FIG. 3.

This novel eEP culture method allows for an increased time window of endodermal gene expression and in vitro cell expansion to generate additional transplantable cells, including those tissues that would benefit from those organs/tissues of endodermal origin, such as liver, lung, pancreas, thyroid, and bladder. As such, these pluripotent stem cell derivatives can be used as a therapeutic for transplantation of cells for organ of endodermal origin. Phenotypically, it was found that: (1) the eEP performs better in transplantation to the liver, judged by the highest level of human albumin in mouse blood, and (2) MIXL1 expression levels are different between the EP and eEP.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), property(ies), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skill in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

To aid the Patent Office, and any readers of any patent issued on this application in interpreting the claims appended hereto, applicants wish to note that they do not intend any of the appended claims to invoke paragraph 6 of 35 U.S.C. § 112, U.S.C. § 112 paragraph (f), or equivalent, as it exists on the date of filing hereof unless the words "means for" or "step for" are explicitly used in the particular claim.

For each of the claims, each dependent claim can depend both from the independent claim and from each of the prior dependent claims for each and every claim so long as the prior claim provides a proper antecedent basis for a claim term or element.

REFERENCES

1. Fagg, W. S., Liu, N., Yang, M. J., Cheng, K., Chung, E., Kim, J. S., Wu, G., and Fair, J. (2017). Magnetic Targeting of Stem Cell Derivatives Enhances Hepatic Engraftment into Structurally Normal Liver. Cell Transplant 26, 1868-1877.
2. Fair, J. H., Cairns, B. A., Lapaglia, M. A., Caballero, M., Pleasant, W. A., Hatada, S., Kim, H. S., Gui, T., Pevny, L., Meyer, A. A., et al. (2005). Correction of factor IX deficiency in mice by embryonic stem cells differentiated in vitro. Proc Natl Acad Sci USA 102, 2958-2963.

3. Loh, K. M., Ang, L. T., Zhang, J., Kumar, V., Ang, J., Auyeong, J. Q., Lee, K. L., Choo, S. H., Lim, C. Y., Nichane, M., et al. (2014). Efficient endoderm induction from human pluripotent stem cells by logically directing signals controlling lineage bifurcations. Cell Stem Cell 14, 237-252.

What is claimed is:

1. A method of preparing differentiated endodermal cells comprising:
   growing human pluripotent stem cells (hPSC) under serum free conditions for 3 days on a layer of fibronectin or a gelatinous protein layer in the presence of activin, a transforming growth factor (TGF-β), or both;
   a glycogen synthase kinase 3 (GSK3) inhibitor; and
   a phosphoinositol 3-kinase (PI3K) inhibitor, a mammalian target of rapamycin complex (mTORC) inhibitor, or both in a basal differentiation medium;
   adding a serum-free replacement to the media starting on day 4 through day 7; and
   harvesting the endodermal cells grown therein, wherein the endodermal cells maintain a stable endodermal precursor gene expression profile for 5 days.

2. The method of claim 1, wherein the GSK3 inhibitor is 6-((2-((4-(2,4-Dichlorophenyl)-5-(4-methyl-1H-imidazol-2-yl)pyrimidin-2-yl)amino)ethyl)amino)nicotinonitrile (CHIR99021).

3. The method of claim 1, wherein the PI3K/mTORC inhibitor is 3-(4-morpholinopyrido[3',2':4,5]furo[3,2-d]pyrimidin-2-yl)phenol (PI-103).

4. The method of claim 1, further comprising the step of changing the media daily during days 1 to 3, days 4 to 7, or both.

5. The method of claim 1, wherein the basal differentiation media comprises 50% Iscove's modified Dulbecco's medium (IMDM) and 50% F12 supplemented with 1 mg/mL polyvinyl alcohol, 1% v/v lipids, monothioglycerol, 0.7 g/mL insulin, and 15 g/mL transferrin.

6. The method of claim 1, wherein the GSK3 inhibitor is maintained in the media after day 1.

7. The method of claim 1, wherein the endodermal cells differentiated have a change in the MIXL1 phenotype after day 7.

8. The method of claim 1, wherein the endodermal cells are transplant competent after 4, 5, 6, or 7 days.

9. The method of claim 1, further comprising the step of transplanting the differentiated endodermal cells into a liver, lung, pancreas, thyroid, or bladder.

10. A method of transplanting endodermal cells into an animal comprising:
    identifying an animal in need of endodermal cell transplantation;
    growing human pluripotent stem cells (hPSC) under serum free conditions for 3 days on a layer of fibronectin or a gelatinous protein layer in the presence of activin, TGF-β, or both;
    a GSK3 inhibitor; and
    a PI3K inhibitor or an mTORC inhibitor, or both in a basal differentiation medium;
    adding a serum-free replacement to the media starting on day 4 through day 7;
    harvesting the endodermal cells grown therein, wherein the endodermal cells maintain a stable endodermal precursor gene expression profile for 5 days; and
    transplanting the endodermal cells into the animal.

11. The method of claim 10, wherein the GSK3 inhibitor is 6-((2-((4-(2,4-Dichlorophenyl)-5-(4-methyl-1H-imidazol-2-yl)pyrimidin-2-yl)amino)ethyl)amino)nicotinonitrile (CHIR99021).

12. The method of claim 10, wherein the PI3K/mTORC inhibitor is 3-(4-morpholinopyrido[3',2':4,5]furo[3,2-d]pyrimidin-2-yl)phenol (PI-103).

13. The method of claim 10, further comprising the step of changing the media daily during days 1 to 3, days 4 to 7, or both.

14. The method of claim 10, wherein the basal differentiation media comprises 50% IMDM and 50% F12 supplemented with 1 mg/mL polyvinyl alcohol, 1% v/v lipids, monothioglycerol, 0.7 g/mL insulin, and 15 g/mL transferrin.

15. The method of claim 10, wherein the GSK3 inhibitor is maintained in the media after day 1.

16. The method of claim 10, wherein the endodermal cells differentiated have a change in the MIXL1 phenotype after day 7.

17. The method of claim 10, wherein the endodermal cells are transplant competent after 4, 5, 6, or 7 days.

18. The method of claim 10, wherein the differentiated endodermal cells are transplanted into a liver, lung, pancreas, thyroid, or bladder.

19. The method of claim 10, wherein the differentiated endodermal cells are liver, lung, pancreas, thyroid, or bladder cells.

20. A method of preparing differentiated endodermal cells made by growing human pluripotent stem cells (hPSC) under serum free conditions on a layer of fibronectin or a gelatinous protein layer in the presence of activin, TGF-β, or both;
    a GSK3 inhibitor; and
    a PI3K inhibitor, or an mTORC inhibitor, or both in a basal differentiation medium followed and adding a serum-free replacement to the media the improvement comprising:
    maintaining the GSK3 inhibitor past day 1 to day 3;
    adding the serum-free replacement to the media starting at day 4 of culture, wherein the differentiated endodermal cells maintain a stable endodermal precursor gene expression profile for 5 days; and
    differentiating endodermal cells for transplant into liver, lung, pancreas, thyroid, or bladder.

* * * * *